United States Patent [19]

Baldeck

[11] 4,208,912
[45] Jun. 24, 1980

[54] GAS SAMPLER/COLLECTOR FOR A MIXTURE OF GASSES

[75] Inventor: Charles M. Baldeck, Columbus, Ohio

[73] Assignee: Industrial Hygiene Specialties, Columbus, Ohio

[21] Appl. No.: 11,954

[22] Filed: Feb. 13, 1979

[51] Int. Cl.² ............................................. G01N 1/22
[52] U.S. Cl. ................................. 73/421.5 R; 422/88
[58] Field of Search .................... 73/421.5 R; 422/88; 55/257 PP

[56] References Cited

U.S. PATENT DOCUMENTS

| 2,097,650 | 11/1937 | Stampe | 422/88 |
| 2,865,720 | 12/1958 | Guild | 422/88 |

FOREIGN PATENT DOCUMENTS 2359040  5/1975  Fed. Rep. of Germany ..... 73/421.5 R

Primary Examiner—S. Clement Swisher
Attorney, Agent, or Firm—Anthony D. Cennamo

[57] ABSTRACT

A gas sampler for sampling a mixture of gasses such as air having toxic gasses or other contaminants, utilizing a vessel with liquid therein as the scrubbing media. The closed vessel comprises intake and exhaust openings for the passage of the sampled gas through the liquid. A hydrophobic porous material sealing the inlet and outlet openings retains the liquid in the vessel without hinderance to the passage of the sampled gas through the liquid. In a preferred embodiment, the vessel comprises a rugged constructed elongated glass tube with open ends. Intermediate the inside of the cap and the open ends of the vessel is positioned the porous hydrophobic material. An operable hydrophobic membrane and alternate capping structures are also disclosed.

10 Claims, 6 Drawing Figures

GAS SAMPLER/COLLECTOR FOR A MIXTURE OF GASSES

Public concern over the deleterious health effects of toxic gases, vapors and other air contaminants has led to the establishment of public laws and health regulations and other standards which apply to occupational exposures in industry, mining and the military, and also to the exposure of the population at large. Compliance with and enforcement of airborne contaminant exposure standards requires methods of measurements which are accurate, reliable, and convenient to use.

Sampling air for gaseous or vapor contaminants is most often done by using a vacuum pump to draw a measured quantity of the air to be sampled through a container having a collection media therein. The collection media can be a solid or a liquid substance which quantitatively absorbs, dissolves or reacts with the air contaminant of interest. The sampling media may then be analyzed by suitable physical and/or chemical methods such as spectrophotometry, gas chromatography or mass spectrography. For some sampling devices and techniques, the gas collector or sampling media may further include its own anlytic elements, such as a colorimetric indicating material.

The most common air sampling device which uses a liquid collection media is the liquid scrubber, impinger or gas washing bottle. In this type of sampler there is a closed vessel, with air inlet and outlet openings, and containing a measured quantity of liquid therein. The air being sampled is drawn in through an intake tube which terminates below the surface of the liquid. The sampled air stream bubbles through the liquid from the end of the intake tube, making direct gas-liquid contact with the collecting or scrubbing liquid, and causing the liquid to be agitated. The contaminants of interest in the sampled air undergo chemical reaction with the liquid which in turn scrubs the air, i.e., removes the contaminants therefrom. The purged air is then expelled or drawn through the exhaust port.

The prior art is familiar with this basic type of sampler and there are commercially available many refined and modified variations thereof. For instance, the gas to liquid contact may be facilitated by bubbling, by deflection, baffling or spraying.

The above mentioned prior art devices for air sampling with a liquid collection media have disadvantages. To avoid contamination and facilitate cleaning they are almost always made of glass; the primary advantage of transparency and non-contamination being a trade-off to the disadvantage of breakage. The air intake and exhaust ports generally comprise appended glass tubular structures, adding to the vessel's fragility. The prior art structures are very easily broken in field sampling use. More importantly, unless the prior art devices are kept upright at all times, the liquid collection media will leak out or be drawn into the sampling pump, voiding the sample and perhaps also ruining the pump. The tendency of the prior art devices to leak also complicates the problem of shipping them with the liquid in place. In practice, the collection liquid is usually added to the vessel in the field, just before use, then quantitatively transferred to a bottle or other container for storage or shipment after use. The practical necessity for transferring liquids at the sampling site causes delays and the possibility of sample contamination. Also with some designs of the prior art liquid media gas samplers, the limited gas-liquid contact area available to scrub the air stream is not entirely satisfactory for optimum mass transfer of the contaminant from the gas to the liquid phase. With, for instance, the aforementioned prior art impinger, some procedures require the use of two or more impingers in series for quantitative contaminant removal.

A few "leakproof" impinger designs are found in the prior art. In these devices, leaking is prevented by use of baffles or traps which prevent liquid from being drawn into the vacuum pump when the device is inverted. These designs are more complex and costly to produce than the ordinary type of scrubbing device, and more subject to the breakage problems.

All of the prior art devices are of a structure which does not lend itself to mass production but must be handmade by a skilled scientific glassblower, which adds to the overall unit cost for a relatively simple device. The problems of prior art vessel leakage, fragility and relatively high unit cost have effectively discouraged the widespread use of liquid media sampling methods for air contaminants, even though such methods have certain inherent advantages, and in some cases are the only proven methods for sampling certain contaminants.

SUMMARY OF INVENTION

A gas sampling article utilizing liquid as the air (gas) scrubbing medium that overcomes the above-noted prior art disadvantages. The preferred embodiment is its simplest form comprises a hydrophobic porous material to retain the scrubbing liquid in the vessel but yet permits the air (gas) to be drawn through the vessel for sampling. The principle of the present invention is equally operable with all prior art vessels having intake and exhaust openings for passage of air (gas) through a liquid and containing a liquid scrubbing medium. The constructed preferred embodiment has structural features that illustrate significant improvements over those of the prior art. The vessel of the present invention comprises a relatively elongated thick glass tube open at both ends. At the ends there is provided means for retaining a cap in sealing engagement with the tube. Each cap has an aperture therein of a size proportioned to the tube opening for the passage of air (gas). Intermediate the inside of the cap and the tube opening is a hydrophobic porous member that retains the liquid in the vessel but yet permits the passage of air.

An operable hydrophobic porous member and alternate structures are illustrated and described. Also to further add to the ruggedness, and make the vessel less fragile, a clear protective sleeve is incorporated over the elongated vessel. The structure is relatively simple, made from standard manufacturing techniques and components, and much less costly than the prior art devices.

OBJECTS

It is a principal object of the present invention to provide an air sampler utilizing liquid as the air scrubbing medium, that is relatively rugged, more efficient and practical for field use, and can be utilized in any manner without liquid spillage.

Another object of the present invention is to provide such a sampler having an operable porous hydrophobic material in sealing engagement with the inlet and outlet openings to retain the liquid in the vessel without leakage, yet allow the free passage of air through the vessel for sampling.

A further object of the present invention is to provide such a sampler that is relatively rugged, can be mass produced with standard-like components, and can be readily transported to and from the sampling site with the liquid media in place without danger of leaking, breakage, or sample contamination.

Other objects and features of the present invention will become apparent from the following detailed description when taken in conjunction with the drawings in which:

DETAILED DESCRIPTION OF DRAWINGS

Figure 1:
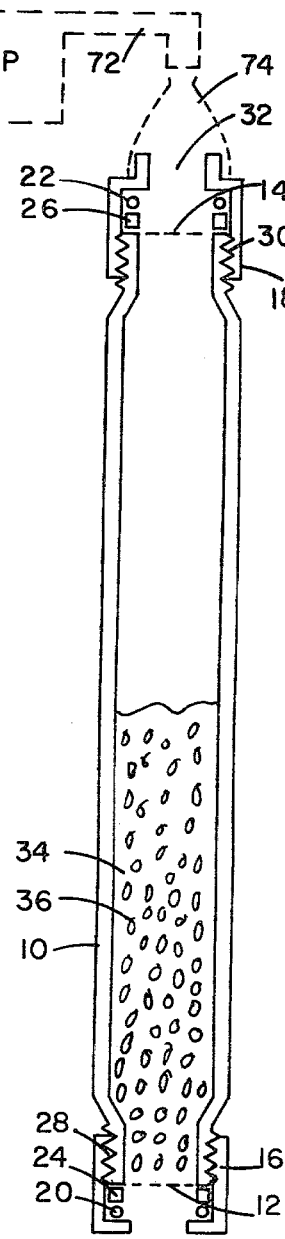
FIG. 1 is a side view in cross-section of a preferred embodiment of the present invention.

With particular reference to FIG. 1 there is illustrated a side view in cross-section of a preferred embodiment of the gas sampler of the present invention. The vessel 10 is an elongated open ended glass tube. Preferably, the vessel 10 is of borosilicate or similarly treated relatively thick glass. At either end of the vessel 10 there is a threaded portion 28 and 30. The overall structure of the vessel 10 is similar to a pair of end-joined screw-capped culture tubes commercially available. Other vessels of divergent shapes and number of openings may also be utilized. The sampler or collector in a constructed embodiment was utilized to sample air for toxic gasses and other contaminants. It is to be understood the invention is not to be so limited and may equally be used for other purposes wherein there is a mixture of gasses and a particular gas is to be separated therefrom.

In threaded engagement with the ends of the vessel 10 are sealing caps 16 and 18. The cap 18 has a port 32 formed thereon for suitably receiving an air-nozzle for the air intake. A hydrophobic porous material 14 is placed intermediate the inside of cap 18 and the one end of the vessel 10; whereas at the other end of vessel 10 a hydrophobic porous material 12 is placed intermediate the inside of cap 16 and the other end of the vessel 10. It is to be noted the cap 16 has an aperture formed therein of a size substantially to that of the end of the vessel 10.

The vessel 10 contains the liquid 34 that provides the scrubbing of the air bubbles 36 upon gas-liquid contact or by other known means.

To assure a liquid tight seal between the caps 16 and 18 and the open ends of the vessel 10, there is a O-ring, 20 and 22, adjacent the inside of the caps 16 and 18 and a washer 24 and 26 of chemically inert material such as polytetrafluoroethylene, adjacent the end of the tubular vessel 10. It can be appreciated that the mechanical configuration for maintaining a liquid seal is within the state of the art. Certain types of caps having washers incorporated therein may also be utilized. A hydrophobic porous membrane material 12 and 14 in one instance was stretched over the ends of the vessel 10 for sealing thereon. This was done by using a small O-ring.

Figure 3:
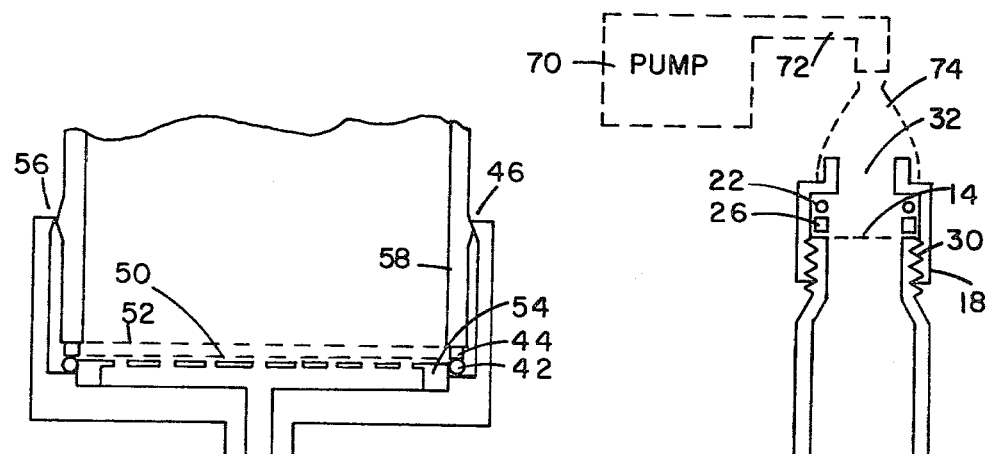
FIG. 3 illustrates in cross-section an alternate capping arrangement.

An alternative design of a cap for supporting and sealing a hydrophobic membrane is illustrated in FIG. 3. In this assembly the cap 48 has a recess 54. The supporting screen 50 has the same outside diameter and a slightly greater depth than that of the recess 54 in cap 48. In this way the screen 50 protrudes slightly from the matching recess 54 to hold the O-ring 42 in position opposite washer 44. The membrane 52 is sealed in this embodiment in a manner similar to that of FIG. 1, that is, between O-ring 42 and washer 44. To assist in aligning the washer 44 the end of the glass vessel has a groove 58 therein for receiving and positioning the washer 44.

Also as shown in FIG. 3 it is to be noted the tubular vessel 98 does not have a threaded end. There is formed on the side of the tubular vessel 98 a bead 46. The cap 48 is of resilient material and has fingers or grippers 56 around the circumference of its extreme end. It can be appreciated the cap assembly is pushed down and snapped into sealing engagement with the end of the tube.

Figure 6:
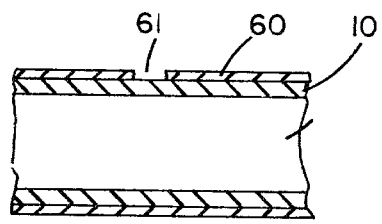
FIG. 6 illustrates in cross-section the protective shield over the glass structure.
Figure 2:
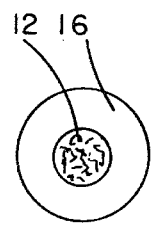
FIG. 2 is a top view of the assembly shown in FIG. 1.

In that cap 48 is resilient the overall structure will be less susceptible to breakage. Together with a non-appended borosilicate tube of glass and resilient end caps the overall structure is substantially more rugged than those of the prior art. However, if the air samplers are to be utilized in an environment where excessive handling would occur, the present invention further provides a clear plastic sheath 60, of FIG. 6, to fit snuggly over the glass tubular vessel 10. In the preferred embodiment the sheath 60 comprised a clear polycarbonate material for viewing the liquid.

The hydrophobic porous members 12 and 14 in the preferred embodiment comprised a 1.0 micron mean pore size membrane filter material made of polytetrafluoroethylene bonded to a high density polyethylene net to provide mechanical strength.

The intrinsically hydrophobic and chemically inert material polytetrafluoroethylene, commonly known as teflon, has been found to be a very suitable material of construction for the hydrophobic porous members 12 and 14. Other porous material, mentioned hereinafter, may also be used if rendered hydrophobic by suitable treatment. For the relatively unhindered passage of the air a mean pore size of at least 0.5 microns is necessary, whereas to completely retain the liquid it was found that the average pore size should be no greater than 20 microns. As known in scrubbers, as those described, the smaller the gas bubbles which are dispersed in the liquid, the greater is the surface area in contact between the two phases, and the greater is the scrubbing efficiency. Accordingly, the mean pore size of the hydrophobic porous material was chosen to be as small as feasible to maximize scrubbing efficiency by optimizing the dispersion of the sampled gas in the liquid scrubbing media.

In operation under test, the hydrophobic porous members 12 and 14 did not leak or pass any liquid water, and the passage of the air through the vessel containing liquid was relatively unimpeded at a vacuum within the capability of most portable sampling pumps. In continuing with the tests, no liquid water leakage could be observed even after violent shaking or repeated inversions of the sampling assembly, even while under vacuum, although during these tests the inertia of the liquid bombarding the membrane did cause the membrane to bulge slightly. Accordingly, under normal intended usage there will be no liquid leakage nor deterioration affects on the hydrophobic material. Again however, since there is no leakage the use of the sampler is extended over those of the prior art providing a similar function. The sampler can be carried, on the person, tilted, strung up or shipped in any manner without leakage.

Figure 5:
FIGS. 4 and 5 show in cross-section a top view of the material makeup and structure of two kinds of hydrophobic membranes.
Figure 5:
Figure 4:
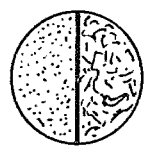

There is shown in FIGS. 4 and 5 in top and side views alternate filter membrane structures that are presently manufactured with a range of pore sizes. The commercially available membranes are available in various constructions and materials, and may take varying dimensions to provide the appropriate pore size. Many of these materials are either intrinsically hydrophobic or can be rendered hydrophobic by appropriate chemical treatment, and some are available commercially so treated.

It is presumed that from time to time other materials and constructions will become available that will be suitable for use as hydrophobic porous members 12 and 14.

In operation of the above-described air sampler, the pump 70 is connected via line 72 to the fitting 74 on the open protrusion 32 of the cap 18. The pump 70 evacuates the air in the vessel 10 and thereby causes an air intake at the opposite end of the vessel 10 through the membrane 12. The air-intake causes air bubbles 36 to rise through the liquid 34. The bubbling action of the air 36 through the liquid 34 "scrubs" the air of gasses and other contaminants. It is understood that other methods and chemical reactions, useful for removing a gaseous component or contaminant from a mixture of gasses such as air by scrubbing through a liquid, and known to those skilled in the art may be utilized without departing from the principles of the present invention. In one such the vessel 10 may further include a colorimetric material for an instant indication of the degree of concentration of the sampled gases. In other applications, the entire vessel 10 with liquid 34 may be taken to the laboratory after sampling for detailed analysis of the collected materials.

It being appreciated that the advantages of a vessel sealed by hydrophobic porous materials can be utilized in most any configuration or application.

The preferred embodiment is an improvement over the prior art in that the structure will not leak the liquid by movement when in use or shipping. The overall structure does not have appendages and therefore would not require special molding dyes in manufacturing. The low cost in turn makes the present invention economical to use for large scale air (gas) sampling investigations where liquid media sampling methods are required. In comparison to the prior art the preferred embodiment is substantially more rugged and less fragile. In that the entire assembly can be prepared and filled in advance, then taken into the field, used and then returned unopened to the laboratory for analysis there is no danger of sample contamination from handling exposed liquids in the field. Finally, the overall structure lends itself more appropriately to the liquid direct-color (gas) titration procedures.

Although only a certain and specific variations of a preferred embodiment are illustrated in a gas/air sampler, it is to be understood that there may be modifications and without departing from the true spirit and scope of the invention.

What is claimed is:

1. Apparatus for sampling gaseous components or contaminants in a gaseous environment utilizing a liquid scrubbing medium comprising:
   a vessel having at least a first and second air (gas) openings for the passage of air (gas) through said vessel,
   a liquid in said vessel for scrubbing said air (gas) of gaseous components or contaminants, and
   a hydrophobic porous material positioned in sealing engagement with said vessel over said openings.

2. The gas sampler of claim 1 wherein said vessel is an elongated tubular structure and said first and second openings are at the ends thereof.

3. The gas sampler of claim 2 wherein said sealing engagement of said hydrophobic material to said tubular structure comprises a cap, said cap having an air passage therethrough and means for engaging the end of said tubular structure.

4. The gas sampler of claim 3 wherein said hydrophobic member further includes a supporting structure and said cap includes sealing washers.

5. The gas sampler of claim 1 wherein said hydrophobic material is a porous structure made of polytetrafluoroethylene.

6. The gas sampler of claim 1 wherein said hydrophobic porous material is a membrane.

7. The gas sampler of claim 5 wherein said hydrophobic material has a mean pore size of 0.5–20 micrometers.

8. The gas sampler of claim 5 wherein said material is self-supporting.

9. The gas sampler of claim 1 wherein said vessel is a glass tube.

10. The gas sampler of claim 9 further comprising a protective covering fitted over said glass.

* * * * *